United States Patent [19]

Roos et al.

[11] Patent Number: 5,296,621
[45] Date of Patent: Mar. 22, 1994

[54] PROCESS FOR THE ISOLATION OF HYDROXY FATTY ACID DERIVATIVES FROM CONVOLVULACEAE PLANTS

[75] Inventors: Robert Roos, Bussum; Jan Bakker, Huizen, both of Netherlands

[73] Assignee: Unilever Patent Holdings B.V., Rotterdam, Netherlands

[21] Appl. No.: 990,935

[22] Filed: Dec. 14, 1992

Related U.S. Application Data

[63] Continuation of Ser. No. 553,404, Jul. 17, 1990, abandoned.

[30] Foreign Application Priority Data

Jul. 20, 1989 [EP] European Pat. Off. ........ 89201920.9

[51] Int. Cl.$^5$ ................................................ C07C 1/00
[52] U.S. Cl. .................................... 554/15; 424/195.1
[58] Field of Search ....................... 554/15; 424/195.1

[56] References Cited

FOREIGN PATENT DOCUMENTS 738420 4/1953 United Kingdom .

OTHER PUBLICATIONS

Wagner et al, Plant Med., vol. 49, No. 3, 1983 pp. 154–157.
Wagner et al, Chemical Abstracts, vol. 100, No. 17, 1983, 135814x.
H. Wagner, The Chemistry of Resin Glycosides of the Convolvulaceae Family, Nobel 25 (1973), Chemistry in botanical classification, pp. 235–240.
Bieber, L. W. et al., Phytochemistry, 1986, vol. 25, No. 5, pp. 1077–1081.
H. Wagner, Planta Medica, 1978, vol. 33, pp. 144–151.
Sukhdev Singh, Phytochemistry, 1973, vol. 12, pp. 1701–1705.
H. Wagner, Phytochemistry, 1977, vol. 16, pp. 715–717.
Tetrahydron Letters No. 36, pp. 3123–3126, 1970.
H. Wagner, Planta Medica 49, (1983), pp. 154–157.
H. Wagner, Planta Medica, 1978, vol. 33, pp. 144–151.
Tetrahydron Letters No. 36, pp. 3123–3126, 1970.

*Primary Examiner*—José G. Dees
*Assistant Examiner*—D. D. Carr
*Attorney, Agent, or Firm*—Cushman, Darby & Cushman

[57] ABSTRACT

The invention provides a process for the isolation of hydroxy fatty acid derivatives from Convolvulaceae plants like *Ipomoea batatas* and *Ipomoea orizabensis* by extracting parts of said plants like leaves, stems, seeds and in particular roots and tubers thereof, with an organic solvent, removing the solvent for at least the main part from the extract, dispersing the obtained residue into water, subjecting the obtained dispersion to a single hydrolysis step and recovering the released hydroxy fatty acids, like 11-hydroxy palmitic acid and 3,11-hydroxy myristic acid from the aqueous dispersion by means of an extraction agent. The obtained hydroxy fatty acid may be used in the synthesis of specific organic compounds like lactones or in the preparation of products having purgative properties and of thickeners for lubricating greases respectively.

15 Claims, No Drawings

PROCESS FOR THE ISOLATION OF HYDROXY FATTY ACID DERIVATIVES FROM CONVOLVULACEAE PLANTS

This is a continuation of application Ser. No. 07/553,404, filed on Jul. 17, 1990, which was abandoned.

BACKGROUND OF THE INVENTION

1. Field of the Invention

The invention relates to a process for the isolation of hydroxy fatty acid derivatives from Convolvulaceae plants by extracting plants like leaves, stems, seeds and in particular roots and/or tubers of said plants with an extraction agent and subsequently subjecting the extraction liquor to a hydrolysis step.

2. Description of the Related Art Including Information Disclosed under 37 CFR §§1.97–1.99

From Planta Medica 9 (1961), the Chemistry of some Convolvulaceous Resins part I, pages 102–116 it is known to isolate Vera Cruz jalap resin from dried tubercles of *Ipomoea purga* Hayne by extracting the substance with alcohol, evaporating off most of the alcohol, pouring the alcoholic liquor into a large volume of water and filtering off the precipitated resin which is then washed with water and dried. Thereupon this jalap resin is divided into an ether insoluble fraction and an ether soluble fraction. Both said fractions are chemically examined by two hydrolysis methods i.e.

a) alkaline hydrolysis using baryta followed by acid hydrolysis and
b) direct acid hydrolysis.

Above method (b) was carried out by dissolving the fraction of the jalap resin in question i.e. the ether soluble fraction or the ether insoluble fraction in ethanol (96%) and acidifying the solution with sulphuric acid until the acid content was about 5%. The ethanolic solution was refluxed for several hours after which most of the alcohol was removed and the residue steam distilled. The remaining aqueous liquor was allowed to stand overnight. During that period a solid matter precipitated which was filtered off or dissolved in chloroform for identification of the obtained hydorxy acids. Dependent on the starting fraction several long chain hydroxy fatty acids could be identified like 3.11-dihydroxy myristic acid and a monohydroxy pentadecanoic acid in the ether insoluble portion and jalapinolic acid (11-hydroxy palmitic acid) in the ether soluble portion.

In Planta Medica 9 (1961), pages 141–145, the Chemistry of some Convolvulaceous Resins part II, the composition of Brazilian jalap resin, obtained from dried sliced tubercles of *Merremia tuberosa* (L) Rendle and of *Operculina macrocarpa* (L) Urban was investigated. The applied investigation method for said resin was based on a subdivision of the resin in an ether insoluble and an ether soluble fraction and then subjecting said fractions to an alkaline hydrolysis followed by an acid hydrolysis. Dependent on the starting fraction several long chain hydroxy fatty acids could be identified like a dihydroxy palmitic acid and probably a trihydroxy myristic acid as well as jalapinolic acid (11-hydroxy palmitic acid).

Further in Planta Medica 9 (1961), pages 146–152, the Chemistry of some Convolvulaceous Resins part III, the composition of Tampico, Ipomoaea and Scammony resins obtained from dried tubercles of *Ipomoea simulans* Hanbury, dried sliced tubercles of *Ipomoea orizabensis* and dried roots of *Convolvulus scammonia* L. respectively were investigated.

Concerning the Tampico jalap resin which was completely soluble in ether, the chemical investigation was carried out by means of an alkaline hydrolysis followed by acid hydrolysis. One of the identified fatty acids was jalapinolic acid.

The Ipomoea resin was divided in an ether insoluble and an ether soluble fraction, which fractions subsequently were subjected to an alkaline hydrolysis and an acid hydrolysis. The same procedure was carried out with Scammony resin. From the results it revealed that said last two resins have to be considered identical and contain several long chain hydroxy fatty acids like jalapinolic acid.

However, from the above it is clear that the isolation methods described in the above references are quite laborous and complicated. For instance several solvents like ether, ethanol and, if required, chloroform are applied.

Summarized it is brought to the fore that the above discussed prior art refer to inadequate methods for isolating the long chain hydroxy fatty acids from the jalap resins or any other suitable source which are not or hardly suitable for use on a large scale. Nevertheless, there is a need for a process for isolating these hydroxy acids on an industrial scale as they are important starting materials for preparing laxatives, lactones and ingredients for lubricating greases.

SUMMARY OF THE INVENTION

Surprisingly it has been found that the long chain hydroxy fatty acids may easily be isolated from the parts of the Convolvulaceae-plants, for instance the leaves, stems, exudates, seeds and in particular the roots and tubers thereof by a) extracting these parts of the Convolvulaceae plants with the help of an organic solvent;
b) removing the solvent for at least the main part and dispersing the obtained material in water, followed by a hydrolysis in a pH-range of 1–9 and
c) recovering the obtained hydroxy fatty acid derivative(s) from the aqueous dispersion.

The merits of the process according to the invention are especially based on the direct hydrolysis of the resin involved in the form of an aqueous dispersion in a pH-range of 1–9 i.e. the necessity of for instance subdividing the resin in an ether soluble and an ether insoluble fraction as well as the application of organic solvents in the hydrolysis step required according to the discussed prior art has become superfluous.

The starting material of the process according to the invention are parts like the roots or tubers of Convolvulaceae-plants growing in several parts of the world. A general survey of said plants is given in R. Hegnauer, Chemotaxonomie der Pflanzen, III, pages 547–561. Examples of suitable Convolvulaceae-plants are species of the genus Ipomoeeae like *Ipomoea orizabensis* (provides Mexican jalap), *Ipomoea batatas* (sweet potato), *Ipomoea turpethum* (provides Indian jalap) and *Ipomoea operaculata* and species of the genus Convolvuleae like *Convolvulus microphyllus*. Examples of suitable hydroxy fatty acids in jalap type resins are:

| | |
|---|---|
| *Ipomoea operculata*: | 3,12-dihydroxypalmitic acid |
| *Ipomoea orizabensis* (Mexican jalap): | 11-hydroxypalmitic acid |
| | 3,11-hydroxymyristic acid |

|  |  |
|---|---|
|  | a hydroxypentadecanoic acid and |
|  | a hydroxylauric acid |
| *Ipomoea turpethum* | 11-hydroxypalmitic acid |
| (Indian jalap): | 3,12-dihydroxypalmitic acid |
|  | 3,12-dihydroxypentadecanoic acid |
| *Convolvulus microphyllus:* | 11-hydroxypalmitic acid |
| *Ipomoea batatas* (sweet potato): | 11-hydroxypalmitic acid |

On account of their availability and composition the roots of *Ipomoea orizabensis* (Mexican jalap) and of *Ipomoea batatas* (sweet potatoes) and/or the residue remaining after the removal of its starch content are preferably applied.

The extraction of the parts of the Convolvulaceae-plants like sliced roots and tubers thereof is carried out with an organic solvent, preferably a "food grade" solvent. Examples of "food grade" solvents are butyl acetate, ethyl acetate, ethanol, acetone, diethyl ether, cyclohexane, butan-1-ol, butan-2-ol, ethylmethylketone, dichloromethane, methyl-propan-1-ol and in particular methyl acetate.

After the complete or partial removal (preferably $\geq 90\%$) of the extraction agent a resin is obtained containing the desired hydroxy fatty acids in esterified form. In view of the fact that the resins per se are not or hardly water soluble it is necessary to disperse the resin in the aqueous hydrolysing medium. This step can easily be carried out with conventional measures like continuous stirring etc.

The acid hydrolysis can be performed in an aqueous solution of an inorganic or organic acid known in the art for this purpose. Examples of such acids are hydrochloric acid, sulphuric acid, phosphoric acid, acetic acid, citric acid, tartaric acid etc.

The hydrolysis time depends on the resin in question, the type of hydrolysis as well as the required hydrolysis ratio but takes normally about 5 hours up to several days, advantageously about 5-20 hours.

The amount of acid necessary for the hydrolysis depends on the resin in question but may vary considerably. A preferred range is about 3-10% by weight of acid, calculated on the total mixture.

The neutral hydrolysis is performed at a temperature between 100° C. and 180° C. and under a pressure between 2 and 20 bar. Preferably the neutral hydrolysis step is carried out at a temperature in a range of from 130°-150° C. and under a pressure between 3 and 6 bar.

Further the hydrolysis may be performed enzymatically. More in particular such an enzymatic hydrolysis step is carried out in a pH-range of 7-9, at a temperature in the range of about 25° to 40° C. and preferably under atmospheric pressure in the presence of an enzyme having esterase activity. Usable enzymes for this purpose, which are generally known in the art, are for instance lipases like pancreas lipase and *Aspergillus niger* lipase.

According to a specific embodiment of the invention the above indicated hydrolysis steps are carried out in an aqueous medium containing a $C_1-C_6$ alkanol like ethanol. Because of the presence of such an alkanol the long chain hydroxy fatty acids in question are obtained in their alkylester-form, in particular their ethylester-form.

The hydrolysis products consist of both water soluble and water insoluble products which last products precipitate. The desired long chain hydroxy fatty acids are present in the precipitated water insoluble material and may be recovered by extracting this material with a suitable extraction agent like nonpolar organic solvents, for instance hexane, cyclohexane, toluene and benzene or by distilling this material under reduced pressure (for instance 0,2-5 mm/Hg) and at elevated temperature (for instance 120°-500° C.).

The hydroxy fatty acids released from parts of the Convolvulaceae-plants do have several applications. For instance said compounds may be used as a lubricating grease ingredient (EP-A-0.244.043) and in the preparation of products having purgative properties. Further said fatty acids may be used in the synthesis of specific organic compounds like lactones.

For evaluating the relative yields of hydroxy fatty acids from several available starting materials, we refer to the following Table:

TABLE A roots of *Ipomoea orizabensis* $\xrightarrow{\text{extraction}}$    I)

16 wt. % resin  $\xrightarrow{\text{hydrolysis}}$
(calc. on roots)

25 wt. % of hydroxy fatty acid(s)
(calc. on resin)

sweet potato (*Ipomoea batatas*) $\xrightarrow{\text{extraction}}$    II)

1 wt. % resin  $\xrightarrow{\text{hydrolysis}}$
(calc. on roots)

25 wt. % of hydroxy fatty acid(s)
(calc. on resin)

The following examples illustrate the process according to the invention; however, the invention is not limited thereto in any way.

A) ISOLATION OF THE RESIN

EXAMPLE 1

1000 g of dried *Radix Scammoniae Mexicanae*, which was previously ground in a grinding cutter (Pallman PS 4-5) was brought into a soxhlet-apparatus and extracted with 5000 ml of methyl acetate for 4 hours at a temperature of 57° C. Then the extract was evaporated under a vacuum of 20 mm Hg and at a temperature of 70° C. The yield was 160 g of resin.

EXAMPLE 2

The process according to Example 1 was repeated, however, with the proviso that at the end of the evaporation stage an amount of 160 g of propylene glycol was added. A liquid solution of resin was obtained which gelled at a temperature of about 35° C. A small increase of temperature reverted the gel to the liquid phase.

EXAMPLE 3

130 g of ground and dried *Radix Scammoniae Mexicanae* was brought into a soxhlet apparatus and extracted with 250 ml of ethanol (96%) at a temperature of 78° C. for 10 hours. Then the extract was evaporated under a vacuum of 20 mm Hg and at a temperature of 70° C. The yield was 15 g of resin.

EXAMPLE 4

927 g of dried slices of *Ipomoea batatas* (sweet potato) was extracted with 3.5 liters of ethanol (96%) at 20° C. for 7 hours under continuous stirring. The extracted sweet potato slices were filtrated and the filtrate was evaporated under a vacuum of 20 mm Hg and at a temperature of 70° C. 66 g of a residue was obtained. This residue was taken up in 200 ml of water and extracted with 200 ml of diethylether. The ether of the ether phase was evaporated under a vacuum of 20 mm Hg and at a temperature of 70° C. The yield was 10 g of resin.

EXAMPLE 5

1000 g of ground and dried *Radix Jalapae Braziliensis* were extracted with 3,5 l of dichloro methane for 6 hours at 20° C. under continuous stirring. After a filtration step, the filtrate was evaporated under a vacuum of 20 mm Hg and at a temperature of 70° C. The yield was 95 g of resin.

B) ISOLATION OF THE HYDROXY FATTY ACIDS

EXAMPLE 6

1000 g of resin obtained according to Example 3 was refluxed in 3 l of water and 500 g of concentrated HCl (37%) under continuous stirring for 12 hours at a temperature of 100° C. After cooling down the liquid water phase was removed by decanting. The solid phase was washed 3 times with water under stirring in order that a HCl-free product was obtained. The remaining solid phase had a weight of about 480 g and contained about 28% of 11-hydroxy palmitic acid. Then the solid phase was washed three times under reflux with a total volume of 3 liters of hexane. The total hexane phase was washed with water and subsequently evaporated under a vacuum of 20 mm Hg and at a temperature of 70° C.

The yield was 142 g of crude 11-hydroxy palmitic acid having a purity of about 90%.

EXAMPLE 7

15 g of resin obtained according to Example 1 was mixed with 10 g of water and subsequently hydrolysed under a pressure of 4–5 bar at a temperature of 140° C. for 12 hours. After cooling down the water phase was removed. The obtained hydrolysis product contained about 3% of 11-hydroxy pelmitic acid. The hydroxy fatty acid was extracted from the hydrolysis product with the help of 100 ml of cyclohexane. The yield was about 0,6 g of crude 11-hydroxy palmitic acid having a purity of about 70%. The non-converted resin can be reused in the hydrolysis stage.

EXAMPLE 8

10 g of resin obtained according to example 1 was mixed with 20 g of water and 1 ml of concentrated $H_3PO_4$ and hydrolysed at 140° C. under a pressure of 4–5 bar for 6 hours. After cooling down the water phase was removed. The obtained hydrolysis product contained about 14% of 11-hydroxy palmitic acid. The hydroxy fatty acid was extracted with 100 ml of hexane. The yield was 2 g of crude 11-hydroxy palmitic acid having a purity of 70%.

EXAMPLE 9

1000 g of resin obtained according to example 1 was hydrolysed according to example 6. The obtained solid having a weight of 480 g and a content of 28% of 11-hydroxy palmitic acid was added to 1500 g of arachis oil at 70° C. Subsequently the oily phase was distilled in a distilling apparatus, type KDL 4 of Leybold Heraeus at 170° C. and under a pressure of 1 mm Hg. The distilling velocity was 300–400 g per hour.

The yield was 120 g of distilled 11-hydroxy palmitic acid having a purity of 95%.

EXAMPLE 10

1000 g of resin obtained according to example 1 added to 3000 ml of ethanol (100%) and 50 ml of concentrated HCl (37%) was refluxed for 12 hours under continuous stirring. Then 1000 g of water was added. After neutralisation with a solution of 10% NaOH in water to a pH-value of 6.5 the excess of ethanol was distilled off under normal pressure. The separated crude ethylester of 11-hydroxy palmitic acid was added to 1500 g of arachis oil at a temperature of 65° C.

The oily phase was washed once with 1000 ml of water and then distilled with the apparatus and under the same conditions described in example 9. The yield was 140 g of distilled ethylester of 11-hydroxy palmitic acid having a purity of 95%.

EXAMPLE 11

10 g of resin obtained according to example 1 was added to 1000 ml of water and emulgated into a fine emulsion with the help of 1 g of cholic acid (sodium salt) Sigma C-1254 and 0.5 g of Tween 80 Sigma P 1754. The emulsion was put in a "pH-apparatus" (i.e. an apparatus designed for maintaining the pH at a specific value). The temperature of the emulsion was adjusted at 38° C. and the pH-value at 8.9. Then 4 g of pancreatine Sigma P-3292 was added. The pH-value was held constant by adding 0.1N NaOH solution. The hydrolysis was stopped after 64 hours.

The reaction mixture was extracted three times with 1000 ml of cyclohexane. The cyclohexane phase was evaporated under normal pressure. The yield was 1.5 g of a crude hydrolysis product having a content of 70% of 11-hydroxy palmitic acid.

We claim:

1. In a process for the isolation of a hydroxy fatty acid or alkyl ester thereof from Convolvulaceae plants by extracting parts of said plants with an extraction agent and subsequently subjecting the extraction liquor to hydrolysis, the improvement which comprises:
   (a) extracting the parts of the Convolvulaceae plants with an organic solvent;
   (b) removing the solvent from at least the main part from the extract to obtain a resinous material containing the desired hydroxy fatty acid in ester form, dispersing the thus obtained material into water and subjecting the obtained dispersion to hydrolysis to form the hydroxy fatty acid or alkyl ester, said hydrolysis selected from the group consisting of:
   (i) acid hydrolysis performed at a temperature in the range of 25° to 180° C. and under a pressure of from 1 up to 25 bar;
   (ii) a neutral hydrolysis performed at a pH of about 7 at a temperature in the range of 25° to 180° and under a pressure of from 1 up to 25 bar; and
   (iii) an enzymatic hydrolysis in the presence of an enzyme having ester activity performed in a pH range of 4-9 at a temperature in the range of 25° to 40° C. under about atmospheric pressure; and c) recovering the resulting hydroxy fatty acid or alkyl ester thereof from the aqueous suspension.

2. Process according to claim 1, wherein species of the genus Ipomoeeae are used as the Convolvulaceae-plants.

3. Process according to claim 1, wherein there are used in stage (a) sliced roots of *Ipomoea orizabensis* or sliced tubers of *Ipomoea batatas* (sweet potato), *Ipomoea turpethum, Ipomoea operaculata* and/or *Convolvulus microphyllus.*

4. Process according to claim 3, wherein there are used in stage (a) sliced roots of *Ipomoea orizabensis* or sliced tubers of *Ipomoea batatas.*

5. Process according to claim 1, wherein there is used in stage (a) a "food grade" solvent as extraction agent.

6. Process according to claim 5, wherein there is used in stage (a) methylacetate as the "food grade" solvent.

7. Process according to claim 1, wherein the hydrolysis is neutral hydrolysis performed at a pH of about 7, at a temperature in the range of from 135° to 145° C. and under a pressure of from 3 to 10 bar.

8. Process according to claim 1 wherein the hydrolysis is an acid hydrolysis performed with the help of hydrochloric acid, sulfuric acid, phosphoric acid, acetic acid, citric acid or tartaric acid or mixtures thereof at a temperature in the range of 100° to 180° C. under a pressure of from about 1 up to 25 bar.

9. Process according to claim 8, wherein the acid hydrolysis step is performed with hydrochloric acid at a temperature in the range of 100°-120° C. and under a pressure of from 1 to 5 Bar.

10. Process according to claim 1, wherein the hydrolysis step is performed in a pH-range of 7-9 and at a temperature in the range of 25° to 40° C. with the help of an enzyme having esterase activity.

11. Process according to claim 10, wherein a lipase is used as the enzyme having esterase activity.

12. Process according to claim 1, wherein stage (c) hexane or cyclohexane is used as extraction agent.

13. Process according to claim 1, wherein the hydroxy fatty acid derivative(s) are recovered in stage (c) by means of a distillation under reduced pressure and at elevated temperature.

14. A process according to claim 1 wherein the plants are Radix Scammoniae Mexicanae plants and the acid obtained is 11-hydroxy palmitic acid.

15. The process of claim 14 wherein the hydrolysis is performed according to (i) in the presence of aqueous ethanol and the desired acid is obtained as the ethyl ester thereof.

* * * * *